United States Patent [19]

Jonkman

[11] Patent Number: 5,782,765
[45] Date of Patent: Jul. 21, 1998

[54] MEDICAL POSITIONING SYSTEM

[75] Inventor: Kenneth R. Jonkman, Grand Rapids, Mich.

[73] Assignee: Medtronic, Inc., Minneapolis, Minn.

[21] Appl. No.: 639,478

[22] Filed: Apr. 25, 1996

[51] Int. Cl.$^6$ ............................................. A61B 5/00
[52] U.S. Cl. ................................. 600/424; 606/130
[58] Field of Search ....................... 600/424, 9, 11, 600/13, 372, 390; 606/130; 128/897, 898, 899, 903

[56] References Cited

U.S. PATENT DOCUMENTS

| | | |
|---|---|---|
| 4,618,978 | 10/1986 | Cosman . |
| 5,084,003 | 1/1992 | Susic ............................ 600/13 |
| 5,309,913 | 5/1994 | Kormos et al. . |
| 5,383,454 | 1/1995 | Bucholz . |
| 5,429,132 | 7/1995 | Guy et al. ...................... 128/653.1 |
| 5,590,655 | 1/1997 | Hussman . |
| 5,662,111 | 9/1997 | Cosman . |
| 5,690,108 | 11/1997 | Chakeres . |

Primary Examiner—Marvin M. Lateef
Assistant Examiner—Shawna J. Shaw
Attorney, Agent, or Firm—Foley & Lardner

[57] ABSTRACT

A method and apparatus for positioning a probe inside a patient including a plurality of transmitter/receiver nodes arranged around the patient for communicating with the probe and generating navigation signals, a system for generating one or more positional signals in response to the navigational signals, and a system for collecting and analyzing those positional signals to determine the location of the medical instrument inside the patient's body. The transmitting/receiving nodes may be arranged on a flexible blanket which is wrapped around and adhered to the patient's body or over a table supporting the patient's body.

12 Claims, 2 Drawing Sheets

5,782,765

1
MEDICAL POSITIONING SYSTEM

BACKGROUND OF THE INVENTION

1. Field of the Invention

This invention relates to a medical positioning system, and more particularly, to a local system for identifying the position of a probe inside a patient's body.

2. Description of the Related Art

Global satellite navigation and positioning systems are well known. For example, the U.S. Navy's TRANSIT system was introduced in the 1960's using seven polar-orbiting satellites which each transmit a beacon-type navigation signal. These satellite signals are used to calculate the position of a ship by comparing the Doppler effect exhibited in the received signal with information concerning the satellite positions which is obtained from another source. The TRANSIT system has been estimated to provide an accuracy of between 20 and 50 meters.

The latest generation of satellite navigational systems, referred to as Global Positioning Systems ("GPS"), was introduced in the late 1970's to provide greater positional accuracy. This next-generation system uses +multilateration techniques to determine a user's position anywhere on earth by analyzing the intersection of several range measurements from simultaneous satellite signals. The current GPS system has been estimated to provide an accuracy of between 15 and 100 meters.

Obviously, positioning a medical device with respect to a patient requires much greater accuracy. Consequently, conventional medical positioning systems have typically included a fixed structure for positioning an instrument relative to various anatomical landmarks on the patient. However, these fixed positioning devices are cumbersome to use and must be repositioned whenever the anatomical landmark is dislocated during the procedure.

SUMMARY OF THE INVENTION

The invention generally relates to a method and apparatus for positioning a probe inside a patient. The apparatus includes a probe for insertion inside a patient, a plurality of transmitter/receiver nodes arranged around the patient for communicating with the probe and generating navigation signals, means for generating one or more positional signals in response to the navigational signals, and means for collecting and analyzing those positional signals to determine the location of the medical instrument inside the patient's body. The nodes may be arranged on a flexible blanket which is provided around the patient's body or may be arranged on a framework surrounding the patient's body. Preferably, the flexible blanket is adhered to the patient's body, or a portion thereof, by a suitable adhesive.

BRIEF DESCRIPTION OF THE DRAWINGS

The invention will now be described with reference to the drawings in which similar features have been labeled with the same reference numerals and.

2
DESCRIPTION OF THE PREFERRED EMBODIMENTS

Figure 1:
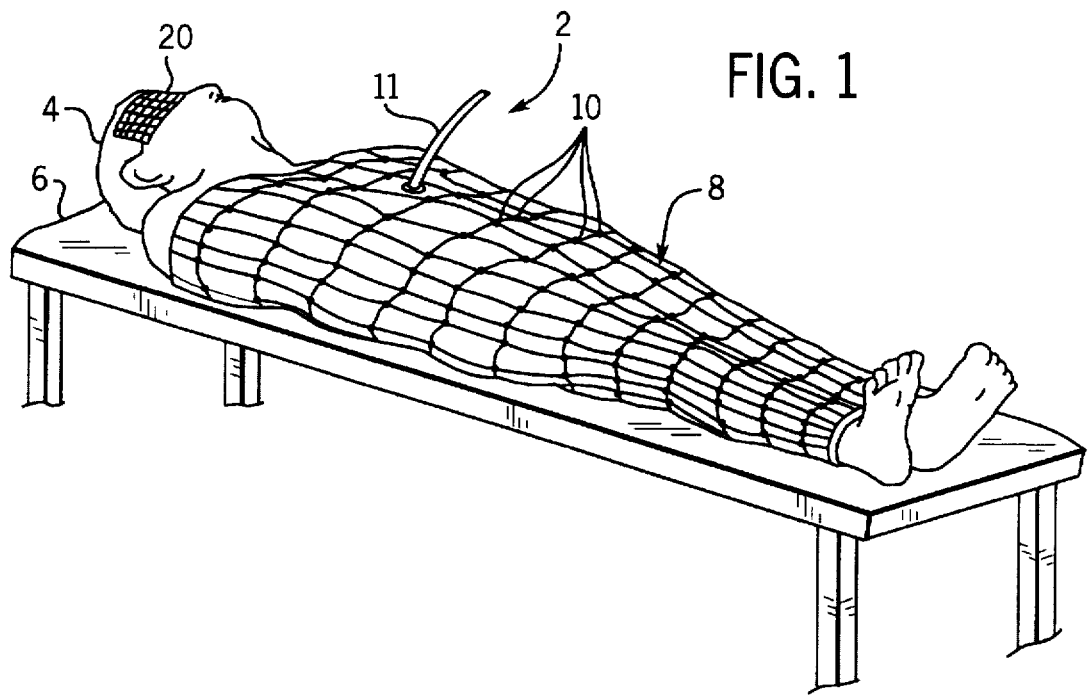
FIG. 1 is a perspective view of a patient who is wrapped in a flexible blanket having a plurality of transmitters/receiver nodes on a probe positioned inside the patient.

Referring now to the drawings, FIG. 1 illustrates a medical positioning system 2 where a patient 4 lies, preferably immobilized by anesthesia, on an examining table 6 while wrapped in a flexible blanket 8 that is attached to the patient so that it does not move relative to the patient. Preferably, the blanket is provided with a suitable adhesive for adhering the blanket 8 to the patient. The blanket 8 is provided with a plurality of transmitter/receiver nodes 10. Each of the nodes 10 will typically include a transmitter or a receiver for communicating with a probe 11 or other medical instrument inserted inside the patient 4. The probe 11 is preferably a laparoscopic probe.

Navigation signals, such as electromagnetic, nuclear, and/or mechanical signals, are transferred between the nodes 10 and the probe 11. In one embodiment, the nodes 10 receive at least one navigation signal from the probe 11. In another embodiment, the nodes 10 transmit at least one navigation signal to the probe 11. In response to receiving these navigation signals, the nodes 10 and/or probe 11 generate one or more positional signals for indicating the position of the probe inside the patient 4.

Figure 2:
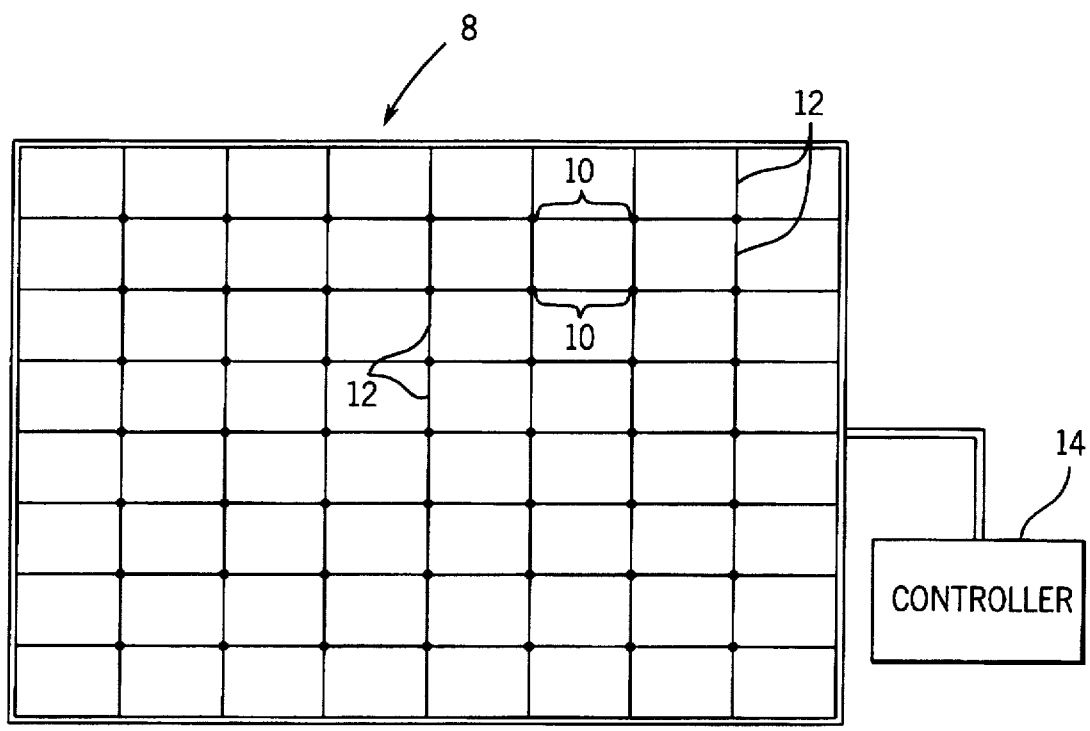
FIG. 2 is a plan view of the flexible blanket and communication network illustrated in FIG. 1.

FIG. 2 is a plan view of the blanket 8 shown in FIG. 1. Positional signals from the transmitter/receiver nodes 10 in the blanket 8 may be sent over a communications network 12 to a controller 14. The probe 11 may also be connected to the controller 14 by the communications network 12 or by another communications network (not shown). The controller 14 analyzes positional signals from the nodes 10 and/or the probe 11 using conventional technology to determine the position of the probe inside the patient's body 4. The position of the probe 11 may be determined relative to an anatomical landmark on the patient 4 or relative to a fixed signal source inside or outside of the patient. The nodes 10 and/or the probe 11 may be self-calibrating.

FIG. 2 also shows an alternative means for providing the transmitter/receiver nodes 10 with a small patch 20 which only surrounds a portion of the patient 4 and can be used for localized applications of the probe 11 and nodes 10. A plurality of patches can be positioned about the patient, or a small patch or blanket can be used to substantially surround a portion of the patient.

Figure 3:
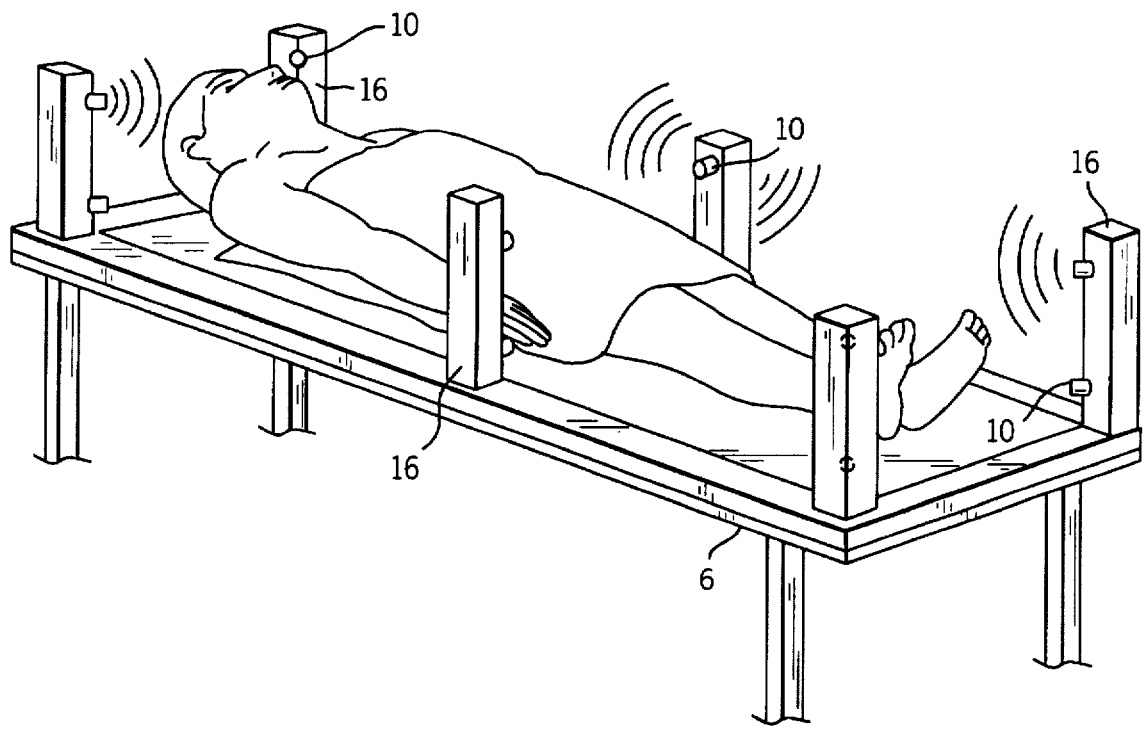
FIG. 3 is a perspective view of a patient on an examining table including a framework of several towers surrounding the patient for supporting the transmitter/receiver nodes.

With reference to FIG. 3, the nodes 10 may be arranged on a framework or towers 16 surrounding the patient 4. One or more nodes 10 may be arranged on each tower 16. Alternatively, the nodes 10 may be arranged on the walls, ceiling, and/or floor of the examining room and/or other rooms in the same building.

During a typical positioning operation, the patient 4 is anesthetized on the table 6. The flexible blanket 8 supporting nodes 10 is wrapped around the patient 4, and the probe 11 is inserted into the patient. For example, the probe 11 may be inserted through the patient's femoral artery for locating an aneurysm or other defect in the patient's aorta. The nodes 10 transmit one or more navigation signals to, or receive one or more navigation signals from, the probe 11 or other medical device (such as a cannula tip) positioned inside the patient 4. Once the position of probe 11 has been precisely located, the physician may easily return to that position using a different instrument, or the physician may precisely aim an energy source at a target inside the patient's body at that position. For example, the system 2 may be used to precisely aim a radiation source at a tumor.

Alternatively, the probe could be used to locate the position of a particular point of tissue, such as a lesion. Once the position has been identified by the controller 14, the surgeon could use the controller to guide the probe or a second surgical instrument back to the original site. Once the controller has determined the position of the probe 11 the first time it is positioned at the desired location, the controller can be used to confirm the position of the probe or surgical tool with respect to this position as the surgeon attempts to return to this position a second time.

Alternatively, the medical device may be used to accurately map the location of various anatomical landmarks inside the patient's body cavity using a minimally invasive procedure. For example, the system 2 could be used to create a three-dimensional contour of a body cavity which is stored by the controller 14 for use in both mapping and tracking. Once the patient 4 is adequately mapped, the controller 14 may also be used to automatically redirect further treatment, such as future radiation treatments.

Reasonable variation and modification are possible within the scope of the foregoing specification and drawings without departing from the spirit of the invention.

The embodiments for which an exclusive property or privilege is claimed are defined as follows:

1. A medical positioning system comprising:
    a probe adapted for insertion into a patient, the probe having one of a transmitter and a receiver provided thereon, the transmitter being adapted for generating a signal and the receiver being adapted to detect the signal;
    a plurality of nodes provided on a flexible framework and arranged to substantially surround at least a portion of the patient, the nodes having the other of the transmitter and receiver provided thereon; and
    a controller electronically connected to the receiver and adapted to interpret the signals received by the transmitter;
    whereby the position of the probe with respect to the plurality of nodes can be determined by interpreting the signals controller.

2. A medical positioning system according to claim 1 wherein the flexible framework comprises a blanket.

3. A medical positioning system according to claim 1 wherein the flexible framework is adhered to at least a portion of the patient by adhesive.

4. A medical positioning system comprising:
    a probe adapted for insertion into a patient, the probe having one of a transmitter and a receiver provided thereon, the transmitter being adapted for generating a signal and the receiver being adapted to detect the signal;
    a plurality of nodes arranged to surround at least a portion of the patient over approximately 360° in a plane passing through the patient, the nodes having the other of the transmitter and receiver provided thereon; and
    a controller electronically connected to the receiver and adapted to interpret the signals received by the transmitter;
    whereby the position of the probe with respect to the plurality of nodes can be determined by interpreting the signals controller.

5. A medical positioning system according to claim 4 wherein the nodes are provided on a flexible framework.

6. A medical positioning system according to claim 5 wherein the flexible framework comprises a blanket.

7. A medical positioning system according to claim 5 wherein the flexible framework is adhered to at least a portion of the patient by adhesive.

8. A medical positioning system according to claim 4 wherein the nodes are provided on a framework.

9. A medical positioning system according to claim 8 wherein the framework comprises a plurality of towers.

10. A medical positioning system comprising:
    a probe adapted for insertion into a patient, the probe having one of a transmitter and a receiver provided thereon, the transmitter being adapted for generating a signal and the receiver being adapted to detect the signal;
    a plurality of nodes provided in a flexible framework blanket, the nodes being arranged around at least a portion of the patient and having the other of the transmitter and receiver provided thereon; and
    a controller electronically connected to the receiver and adapted to interpret the signals received by the transmitter;
    whereby the position of the probe with respect to the plurality of nodes can be determined by interpreting the signals controller.

11. A medical positioning system according to claim 10 wherein the flexible framework is adhered to at least a portion of the patient by adhesive.

12. A medical positioning system comprising:
    a probe adapted for insertion into a patient, the probe having one of a transmitter and a receiver provided thereon, the transmitter being adapted for generating a signal and the receiver being adapted to detect the signal;
    a plurality of nodes provided on a plurality of towers arranged to substantially surround at least a portion of the patient, the nodes having the other of the transmitter and receiver provided thereon; and
    a controller electronically connected to the receiver and adapted to interpret the signals received by the transmitter;
    whereby the position of the probe with respect to the plurality of nodes can be determined by interpreting the signals controller.

* * * * *